(12) United States Patent
Brett (10) Patent No.: US 6,409,766 B1
(45) Date of Patent: *Jun. 25, 2002

(54) COLLAPSIBLE AND EXPANDABLE INTERBODY FUSION DEVICE

(75) Inventor: Darrell C. Brett, Portland, OR (US)

(73) Assignee: Expanding Concepts, LLC, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/635,364

(22) Filed: Aug. 9, 2000

Related U.S. Application Data (63) Continuation of application No. 09/350,984, filed on Jul. 9, 1999, now Pat. No. 6,126,689.
(60) Provisional application No. 60/094,732, filed on Jul. 30, 1998.

(51) Int. Cl.⁷ .................................................. A61F 2/44
(52) U.S. Cl. ................................. 623/17.16; 623/17.15
(58) Field of Search ..................... 606/61; 623/17.11, 623/17.15, 17.16

(56) References Cited

U.S. PATENT DOCUMENTS

| | | |
|---|---|---|
| 4,011,602 A | 3/1977 | Rybicki |
| 5,522,899 A | 6/1996 | Michelson |
| D377,095 S | 12/1996 | Michelson |
| D377,096 S | 12/1996 | Michelson |
| D377,527 S | 1/1997 | Michelson |
| 5,593,409 A | 1/1997 | Michelson |
| 5,749,916 A | 5/1998 | Richelsoph |
| 5,776,199 A | 7/1998 | Michelson |
| 5,782,832 A | 7/1998 | Larsen et al. |
| 5,785,710 A | 7/1998 | Michelson |
| 6,045,579 A | 4/2000 | Hochshuler et al. |
| 6,080,193 A | 6/2000 | Hochshuler et al. |
| 6,126,689 A | * 10/2000 | Brett ........................ 623/17.16 |

OTHER PUBLICATIONS

Curtis Dickman, MD; Internal Fixation and Fusion of the Lumbar Spine Using Threaded Interbody Cages; BNI Quarterly; 1997; 4–25; vol. 13, No. 3.

Spine magazine advertisement re Spinal Concepts'InFix Interbody Fusion System, at least as early as Sep. 2000.

* cited by examiner

Primary Examiner—Paul J. Hirsch
(74) Attorney, Agent, or Firm—Karen Dana Oster (57) ABSTRACT

A collapsible and expandable interbody fusion cage primarily for use between adjacent vertebrae is designed to be collapsed so as to require the smallest opening necessary for insertion. An upper body is connected to a lower body by articulated supports. In the collapsed position, the articulated supports are folded inward between the upper body and the lower body. Once inserted, the fusion cage can be expanded to its fully open position to maintain spacing between adjacent vertebrae. The fusion cage is maintained in its fully open position by an overcenter latch. Bone material can be inserted in the space formed by the fully open fusion cage to aid in the fusion of the adjacent vertebrae.

17 Claims, 10 Drawing Sheets

COLLAPSIBLE AND EXPANDABLE INTERBODY FUSION DEVICE

The present application is a continuation of U.S. Utility patent application Ser. No. 09/350,984, filed Jul. 9, 1999, now U.S. Pat. No. 6,126,689 which claimed the benefit of U.S. Provisional Patent Application Serial No. 60/094,732, filed Jul. 30, 1998, for a Collapsible and Expandable Interbody Spinal Fusion Device.

BACKGROUND OF THE INVENTION

This invention relates to bone fusion devices. More specifically, it relates to devices that fuse spinal vertebrae together.

Fusion cages provide a space for inserting a bone graft between adjacent portions of bone. In time, the bone and bone graft grow together through or around the fusion cage to fuse the graft and the bone solidly together. One current use of fusion cages is to treat a variety of spinal disorders, including degenerative disc diseases such as Grade I or II spondylolistheses of the lumbar spine. Spinal fusion cages (included in the general term, "fusion cages") are inserted into the intervertebral disc space between two vertebrae for fusing them together. They distract (or expand) a collapsed disc space between two vertebrae to stabilize the vertebrae by preventing them from moving relative to each other.

The typical fusion cage is cylindrical, hollow, and threaded. Alternatively, some known fusion cages are unthreaded or made in tapered, elliptical, or rectangular shapes. Known fusion cages are constructed from a variety of materials including titanium alloys, porous tantalum, other metals, allograft bone, or ceramic material.

Fusion cages may be used to connect any adjacent portions of bone, however one primary use is in the lumbar spine. Fusion cages can also be used in the cervical or thoracic spine. Fusion cages can be inserted in the lumbar spine using an anterior, posterior, or lateral approach. Insertion is usually accomplished through a traditional open operation, but a laparoscopic or percutaneous insertion technique can also be used.

With any of the approaches, threaded fusion cages are inserted by first opening the disc space between two vertebrae of the lumbar spine using a wedge or other device on a first side of the vertebrae. Next, a tapered plug is hammered in to hold the disc space open. A threaded opening is then drilled and tapped on a second side opposite the first side of the vertebrae for producing the equivalent of a "split" threaded bore defined by the walls of the vertebrae above and below the bore. The threaded fusion cage is then threaded into the bore and the wedge is removed. The first side is then drilled and tapped before inserting a second threaded fusion cage. Typically, two threaded fusion cages are used at each invertebral disc level.

There are problems with all of the standard approaches. With a posterior approach, neural structures in the spinal canal and foramen need to be properly retracted before the plug is hammered into the disc space. Proper neural retraction is critical to the insertion process. If the retraction is not done properly, the procedure could cause neural injury, i.e., nerve damage and potential neurologic deficit. With either the anterior or lateral approach, blood vessels or other vital structures need to be retracted and protected to reduce or eliminate internal bleeding.

The general technique for inserting fusion cages is well known. Insertion techniques and additional details on the design of fusion cages is described in *Internal Fixation and Fusion of the Lumbar Spine Using Threaded Interbody Cages,* by Curtis A. Dickman, M.D., published in BNI Quarterly, Volume 13, Number 3, 1997, which is hereby incorporated by reference.

U.S. Pat. No. 5,782,832 to Larsen et al. (the "Larsen reference") discloses an alternate type of spinal fusion implant. FIG. 1 of the Larsen reference shows an implant apparatus with two separable support components which are adapted for adjusting sliding movement relative to each other to selectively vary the overall width of the implant to accommodate vertebral columns of various sizes or to vary the supporting capacity of the implant during healing. Each of the support components include upper and lower plate portions that are operatively connected by respective linkage mechanisms. The linkage mechanisms allow relative movement of the upper and lower plate portions between an extended position and a collapsed position. The device disclosed in the Larsen reference has several problems. One problem is that, because the width of the implant is adjusted prior to insertion, a wide insertion slot is necessary despite the reduced profile presented by the collapsed implant. Another problem is that at least part of the linkage mechanism extends beyond the upper and lower plate portions, thus requiring more invasion into the body cavity to position the implant. Yet another problem is that the linkage mechanisms must be locked into the expanded position by conventional arrangements such as locking screws.

The problems discussed above in regard to known fusion cages are substantially solved by the present invention.

BRIEF SUMMARY OF THE INVENTION

The present invention is directed to a fusion cage that can be inserted less intrusively and requires a reduced size opening for insertion than known fusion cages. Reducing the size of the opening reduces and perhaps eliminates the need for retraction of neural structures, vascular structures, or other vital structures. Consequently, compared to known fusion cages, the fusion cage of the present reduces operating time, reduces blood loss, and reduces the risk of injury. It is believed that the present invention provides these and other advantages.

One preferred embodiment of the interbody fusion cage of the present invention includes an upper body and a lower body connected by articulated supports. The articulated supports enable the fusion cage to be collapsed prior to its insertion between adjacent vertebrae. Once inserted, the articulated supports allow the fusion cage to be expanded to a fully expanded position.

In another preferred embodiment, the fusion cage includes protrusions on the articulated supports, or ridges or other surface irregularities along the fusion cage's upper and lower surfaces, to secure the fusion cage in position.

In an alternate preferred embodiment, an overcenter latch mechanism may be incorporated to maintain the fusion cage in the fully expanded position. Buttressing, or stops, located where the articulated supports attach to the upper or lower body, prevents the articulated supports from continuing out past the desired maximum height. Once at the maximum height, the forces exerted on the fusion cage by the bone surfaces above and below it continue to force the articulated supports outward against the stops.

Bone, or other material intended to promote bone growth, can be inserted into the cavity formed by the upper and lower body and the fully extended articulated supports. Eventually, adjacent vertebrae will grow through and around the fusion cage, effectively fusing the two vertebrae together.

DETAILED DESCRIPTION OF THE INVENTION

The several embodiments of the fusion cage according to this invention are shown in the figures. Like numbers correspond to identical or corresponding parts. References to "upper," "lower," "left," "right," or other terms denoting relative position refer to the drawing as shown and are for convenience only as the fusion cage can assume any orientation when in use.

Figure 4:
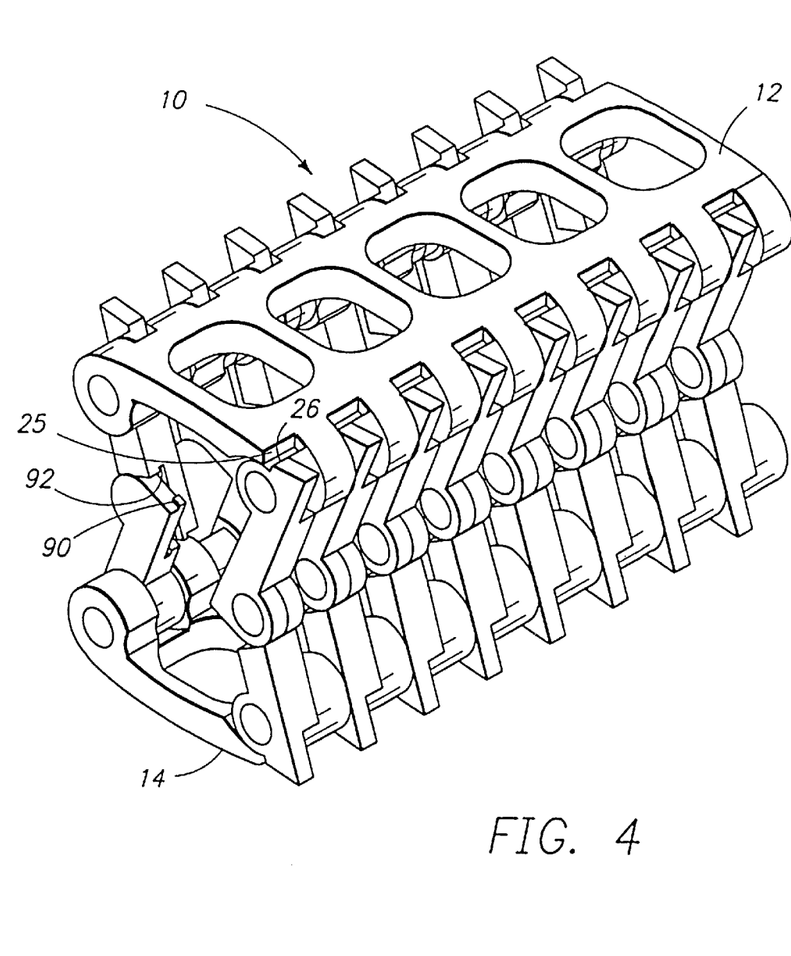
FIG. 4 is a perspective view of a spinal fusion cage in accordance with the present invention in a partially collapsed position.
Figure 5:
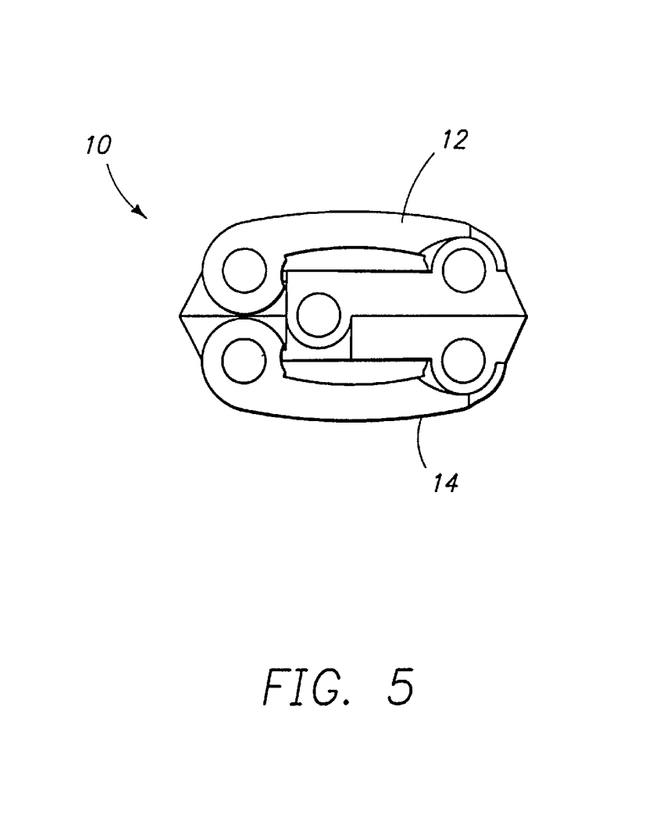
FIG. 5 is an end view of a spinal fusion cage in accordance with the present invention in a fully collapsed position.
Figure 6:
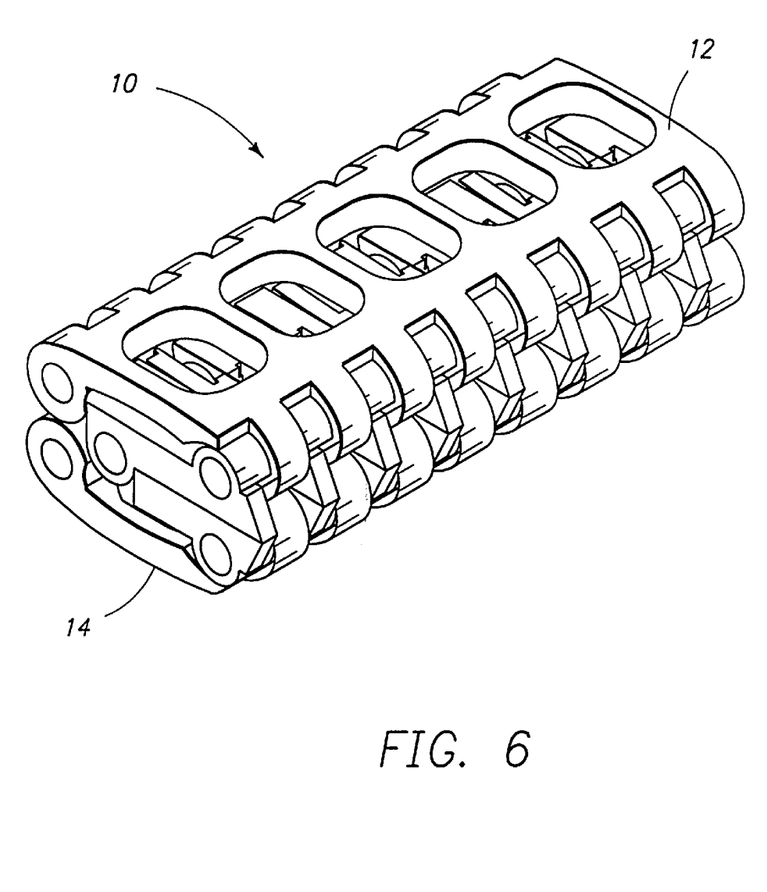
FIG. 6 is a perspective view of a spinal fusion case in accordance with the present invention in a fully collapsed position.

A fusion cage 10 of the present invention includes an upper body 12 connected to a lower body 14 by side articulated supports 16, 18. The fusion cage 10 expands and contracts between a fully open or expanded position (FIGS. 1 and 2), through a midway, partially collapsed position (FIGS. 3 and 4), to a fully closed or collapsed position (FIGS. 5 and 6). This ability to expand and collapse allows the fusion cage to be inserted through a much smaller opening than is possible with rigid fusion cages, while providing the same final spacing between the vertebrae as provided by rigid fusion cages.

Figures 1, 2:
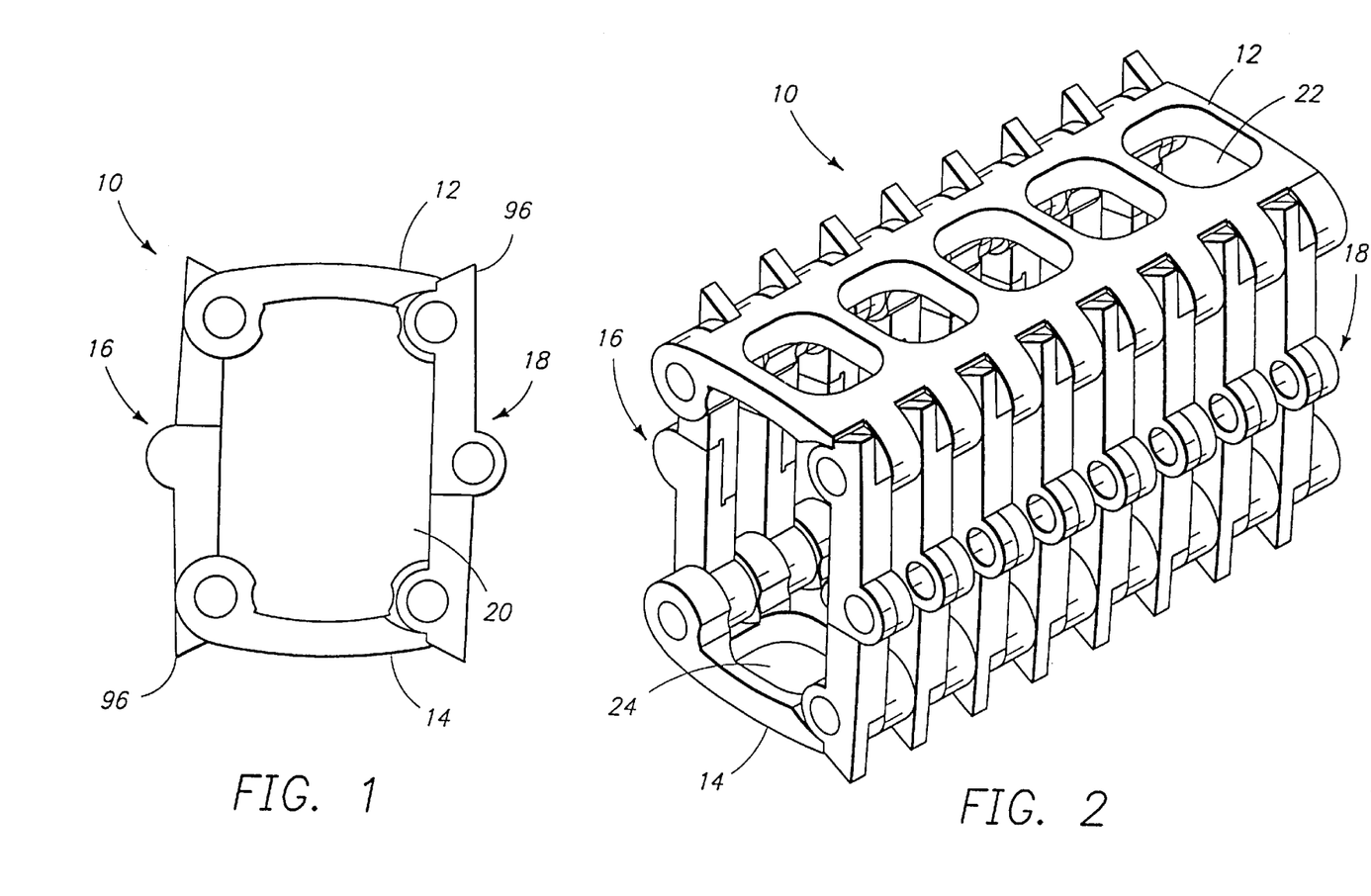
FIG. 1 is an end view of a spinal fusion cage in accordance with the present invention in a fully expanded position.
FIG. 2 is a perspective view of a spinal fusion cage in accordance with the present invention in a fully expanded position.

When in the open position, as shown in FIGS. 1 and 2, the upper body 12, the lower body 14, and the articulated supports 16 and 18 form a hollow cavity 20 adapted to contain autologous bone, artificial bone, bone matrix, bone growth proteins, or other materials (not shown).

The upper body 12 has a series of openings 22 to allow ingrowth of vertebrae bone and vasculature through the opening and into the hollow cavity 20. Likewise, the lower body 14 has a series of openings 24 to allow ingrowth of bone into the hollow cavity 20 from below.

The left-side articulated supports 16 are arranged substantially parallel to each other. The right-side articulated supports 18 are also arranged substantially parallel to each other and parallel to the left-side articulated supports 16 when the fusion cage is in the open position. The right-side articulated supports 18 are positioned with an offset relative to the left-side articulated supports 16 so that they can effectively pass between the left-side articulated supports as the fusion cage 10 is collapsed. The center, joint or hinged part (described further below) of the side articulated supports 16, 18 become interdigitated or juxtaposed ("interdigitated supports") when the fusion cage 10 is fully collapsed.

Figures 7, 8:
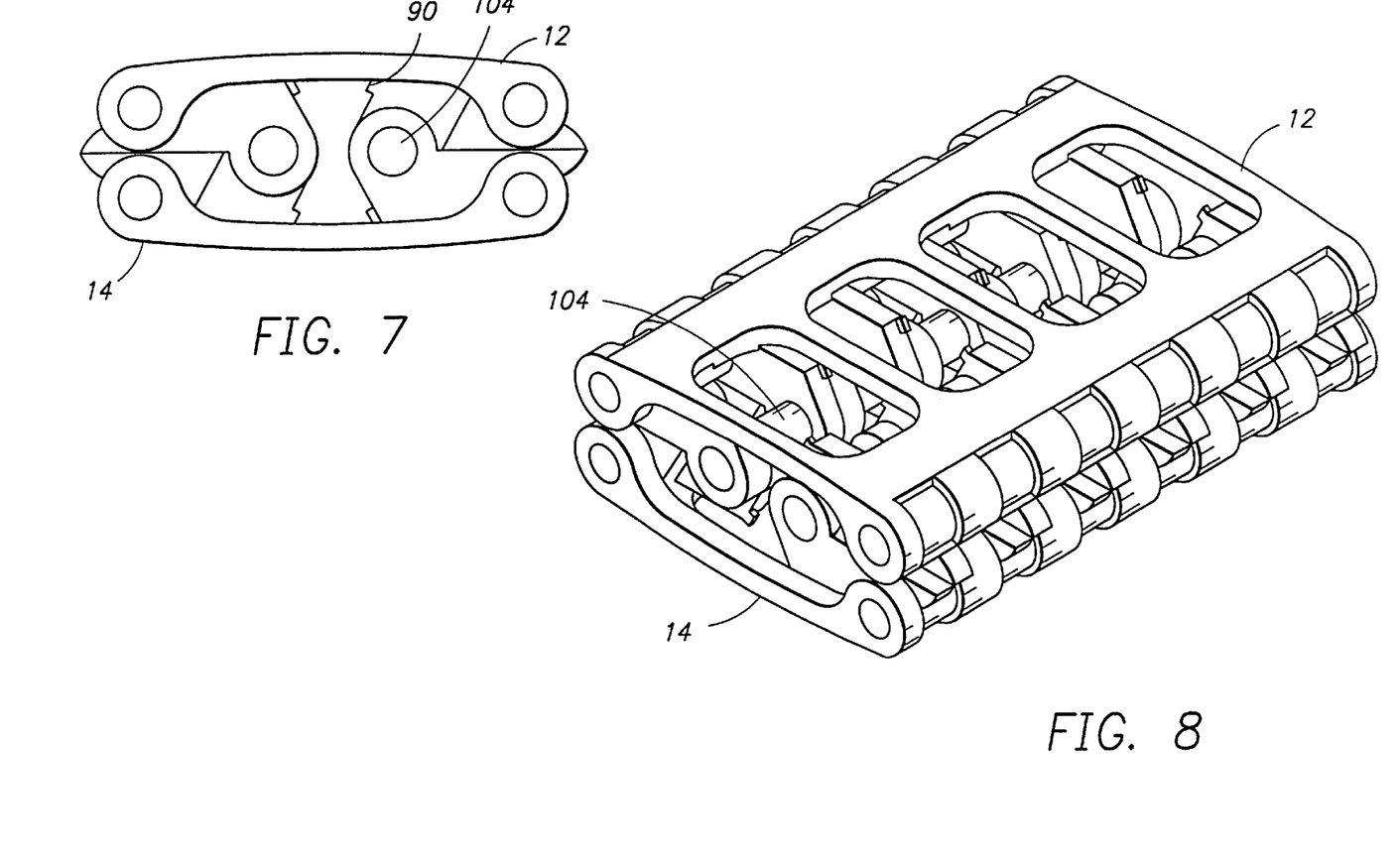
FIG. 7 is an end view of an alternative embodiment of the fusion cage in a fully collapsed position.
FIG. 8 is a perspective view of an alternative embodiment of the fusion cage in a fully collapsed position.

It should be noted that, although interdigitated supports are a feature of a preferred embodiment, the interdigitation is an optional feature. As shown in FIGS. 7 and 8, in some applications the maximum height relative to the collapsed height will be sufficiently small to allow the articulated supports to collapse inward without interfering with each other. In such cases, there is no need to offset the left and right articulated supports, and a single long pin 104 can be used to connect the upper legs 60 to the lower legs 62.

Figure 9:
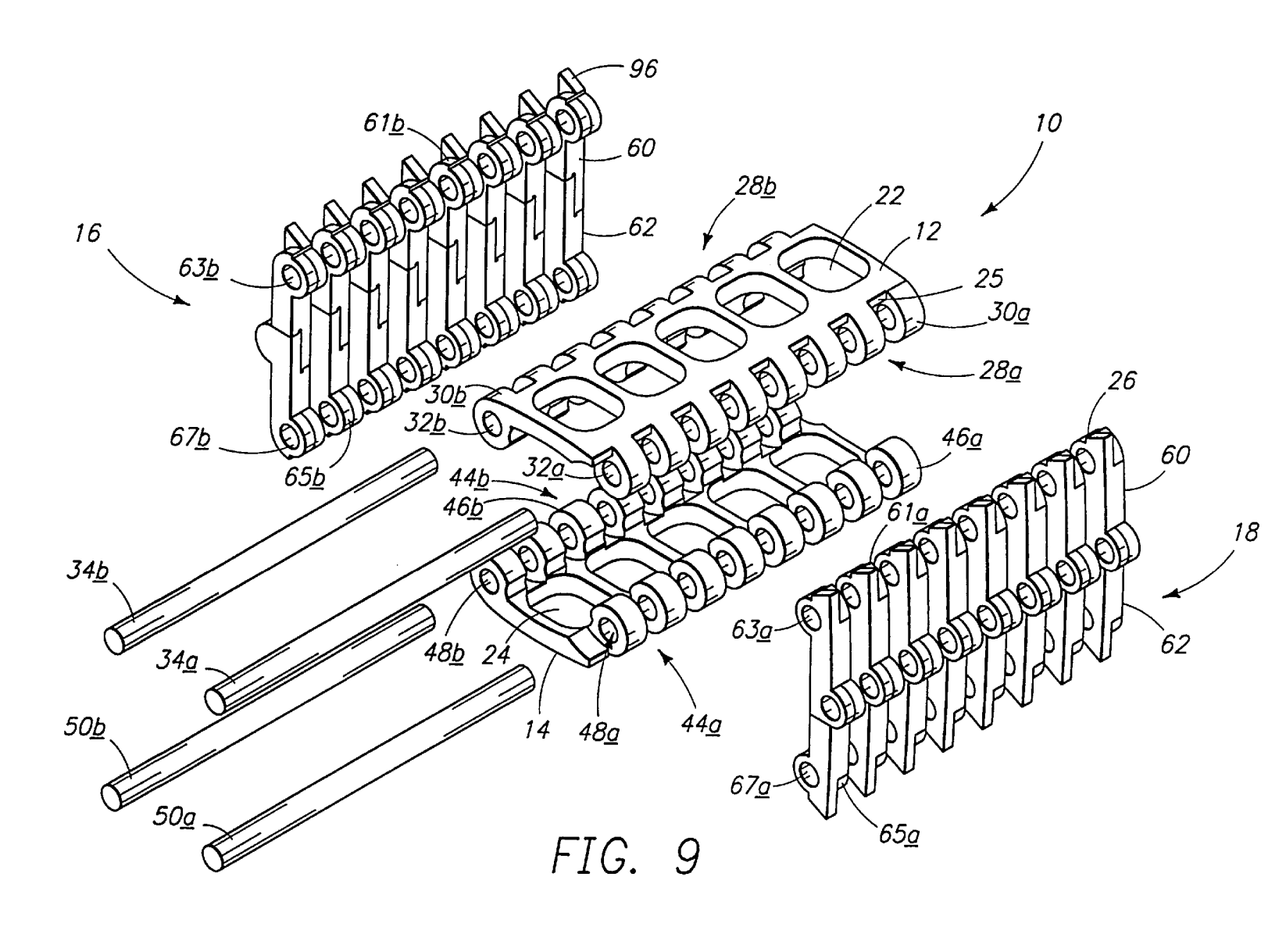
FIG. 9 is an exploded view of a spinal fusion cage in accordance with the present invention.

Referring to FIG. 9, the upper body 12 has side edges 28a, 28b, each side edge 28a, 28b having a plurality of axially aligned hinge knuckles 30a, 30b. The knuckles 30a, 30b each have an axially extending bore 32a, 32b defined therethrough for receiving a pintle 34a, 34b. Likewise the lower body 14 has corresponding side edges 44a, 44b, each side edge 44a, 44b having a plurality of hinge knuckles 46a, 46b that form parallel, axially extending bores 48a, 48b for receiving a second pintle 50a, 50b. Each articulated support 16, 18 has an upper leg 60 and a lower leg 62 pivotally connected to each other. Each upper leg 60 has a hinge knuckle 61a, 61b with a bore 63a, 63b that fits between two of the upper hinge knuckles 30a, 30b in alignment with bore 32a, 32b for receiving pintles 34a, 34b. Each lower leg 62 has a hinge knuckle 65a, 65b with a bore 67a, 67b that fits between two of the lower hinge knuckles 46a, 46b in alignment with bore 48a, 48b for receiving pintles 50a, 50b. The knuckle and pintle structure allows the articulated supports 16, 18 to interconnect the upper and lower bodies 12, 14.

FIGS. 10–13 show exemplary articulated supports according to two embodiments of the fusion cage. Each exemplary articulated support 16, 18 has an upper leg 60 pivotally connected to a lower leg 62. The legs 60, 62 have hinge knuckles 61, 65 with respective bores 63, 67 suitable for the knuckle and pintle structure described above.

Figure 10:
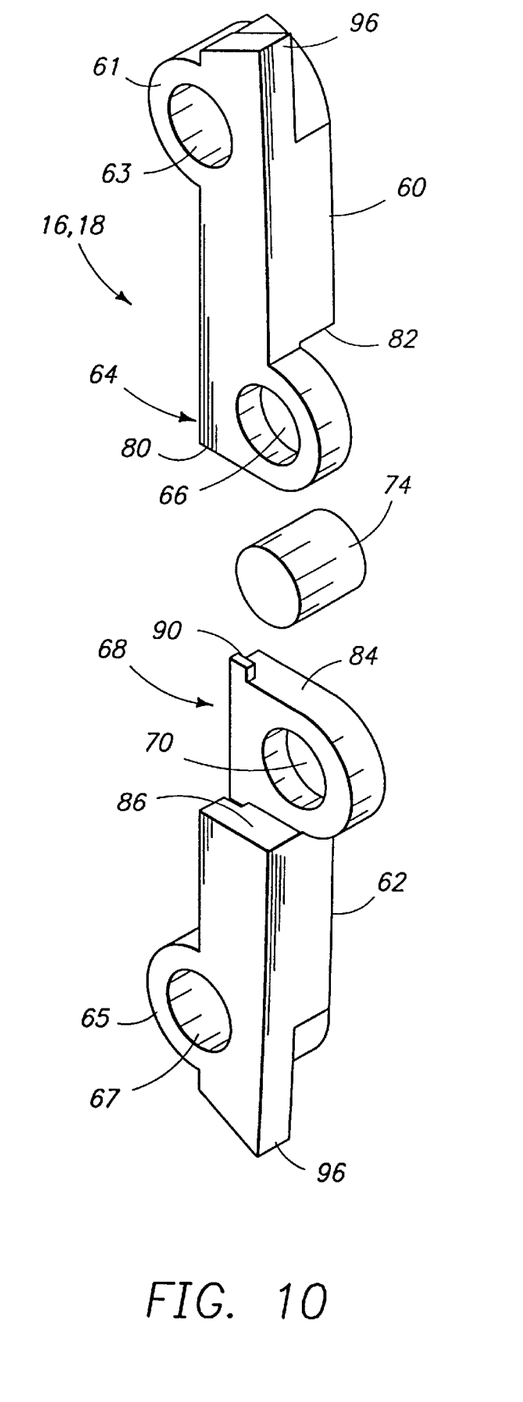
FIG. 10 is an exploded view of one embodiment of an articulated support utilizing a pin in accordance with the present invention.
Figure 11:
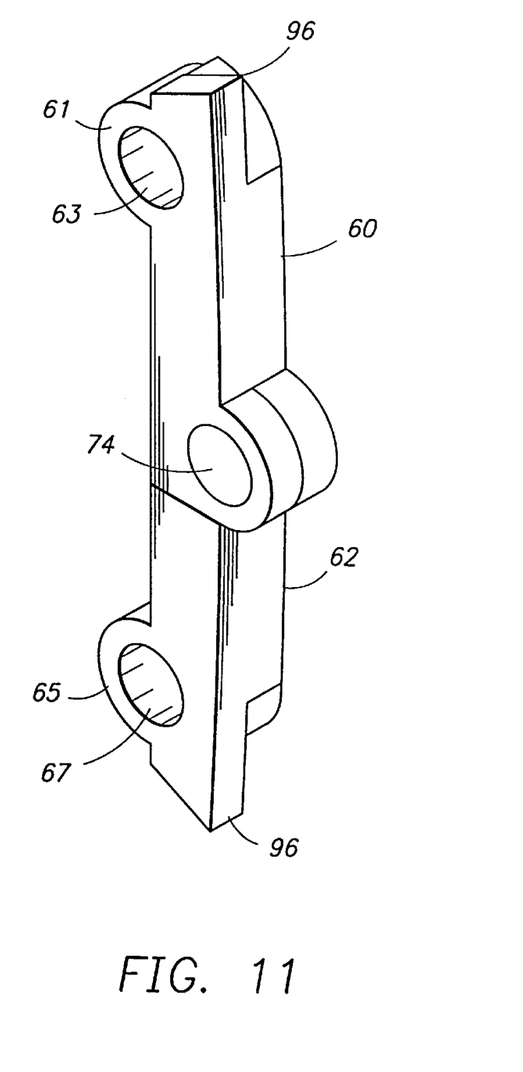
FIG. 11 is a perspective view of the assembled articulated support of FIG. 10.

FIGS. 10 and 11 show one exemplary embodiment of an articulated support 16, 18. In this embodiment, the upper leg 60 has a lower end 64 with a pin hole 66 defined therein. The lower leg 62 has an upper end 68 with a complementary pin hole 70. These pin holes 66, 70 are aligned and pivotally connected by a short pin 74. The lower end of the upper leg 60 has a shelf 80 and a ledge 82. Likewise, the upper end of the lower leg 64 has a shelf 84 and a ledge 86. When the fusion cage is in the fully opened position, the shelf 80 of the upper leg engages the ledge 86 of the lower leg, and the shelf 84 of the lower leg engages the ledge 82 of the upper leg. The engagement of ledges and shelves provides added support when the fusion cage is in the fully open position and prevents the articulated supports from opening past the desired position. In a preferred embodiment, a tab 90 is provided to fit tightly within a corresponding notch 92 (FIG. 4). The tab 90 engaged within the notch 92 assists in maintaining the articulated supports in an overcenter position by increasing the force necessary to recollapse the articulated supports inward.

Figure 12:
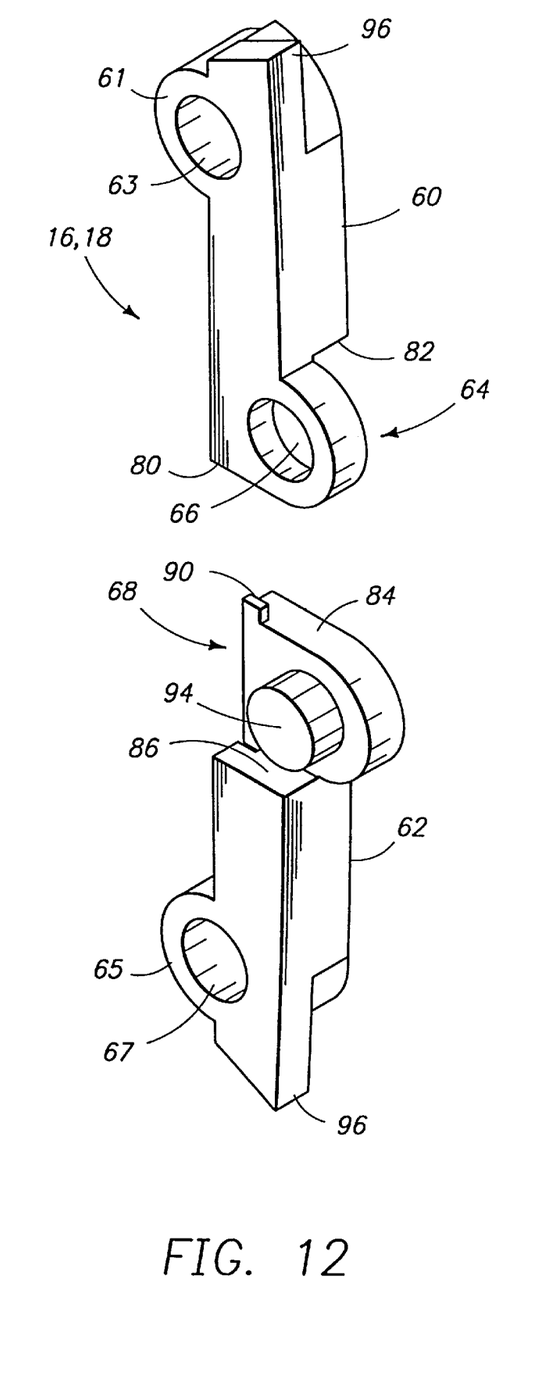
FIG. 12 is an exploded view of an alternative embodiment of an articulated support utilizing a post in accordance with the present invention.
Figure 13:
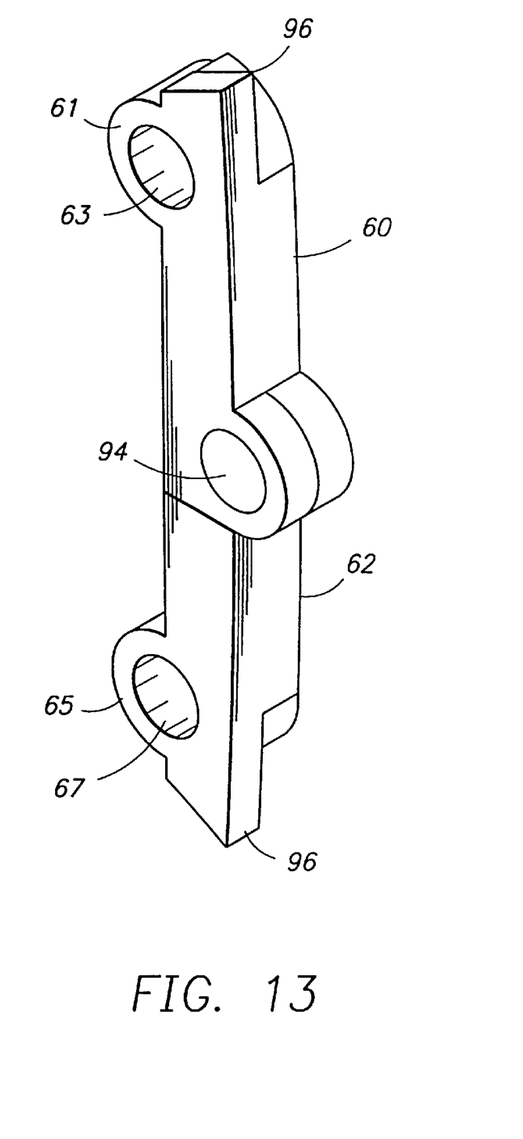
FIG. 13 is a perspective view of the assembled articulated support of FIG. 12.

FIGS. 12 and 13 show an alternate exemplary embodiment of an articulated support 16, 18. In this embodiment, the upper end 68 has a post 94 instead of pin hole 66. The lower end 64 continues to have pin hole 66, defined therein. The post 94 pivotally mates with the pin hole 66. This structure eliminates the need for the separate short pin 74. The ledge and shelf structure and the tab and notch structure may be repeated in this embodiment.

Figure 14:
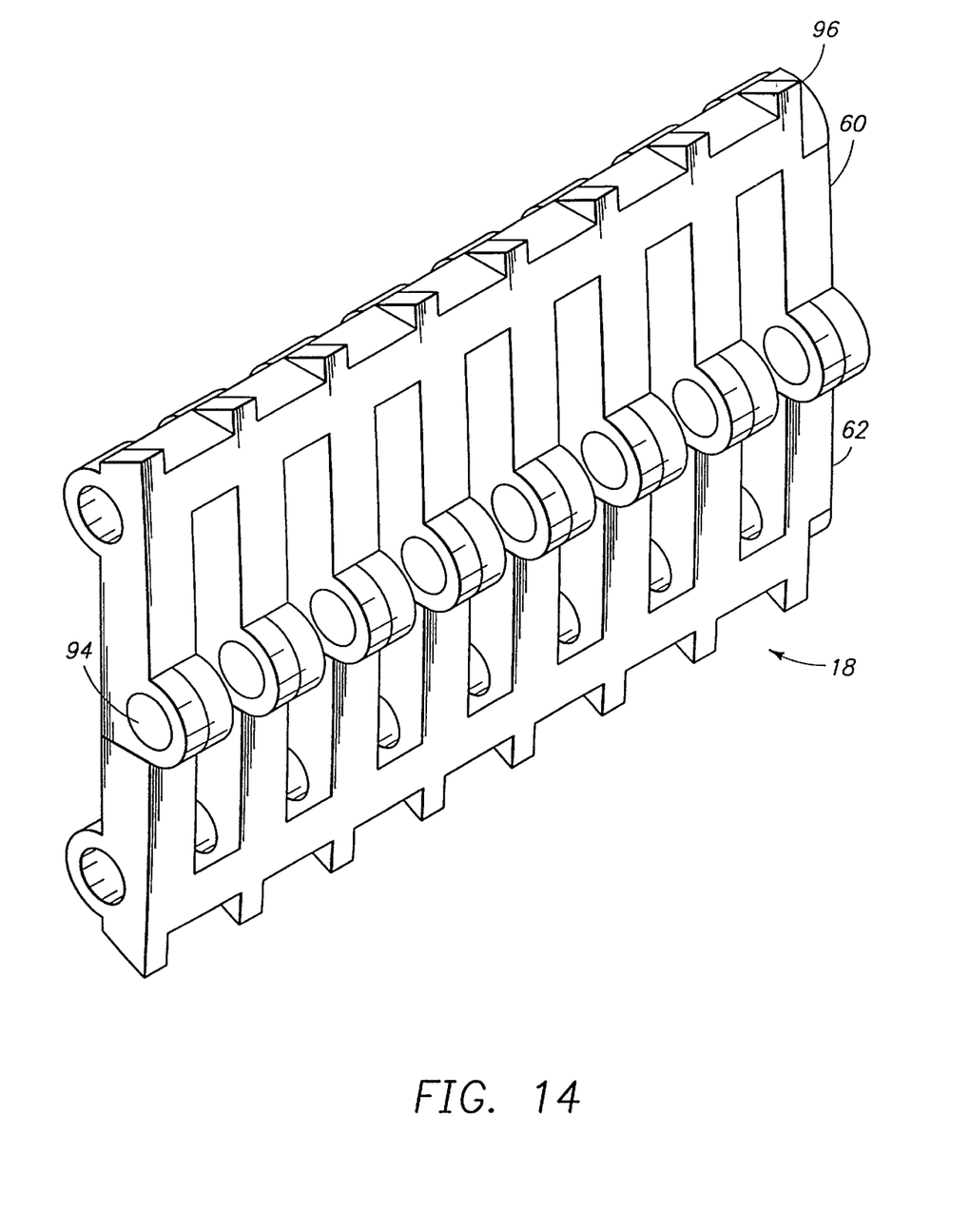
FIG. 14 is a perspective view of an alternative preferred embodiment of the articulated supports.

Although the figures show a device having sixteen articulated supports, it would be possible to utilize fewer articulated supports. Each articulated support would then need to be designed to support additional weight. The use of fewer articulated supports along with a post and hole instead of a separate pin would reduce the number of components and improve manufacturing efficiency. The upper legs could also be joined together near the hinge knuckle to form a single upper leg unit as shown in FIG. 14, further reducing the overall piece count. The lower legs could likewise be joined.

Figure 15:
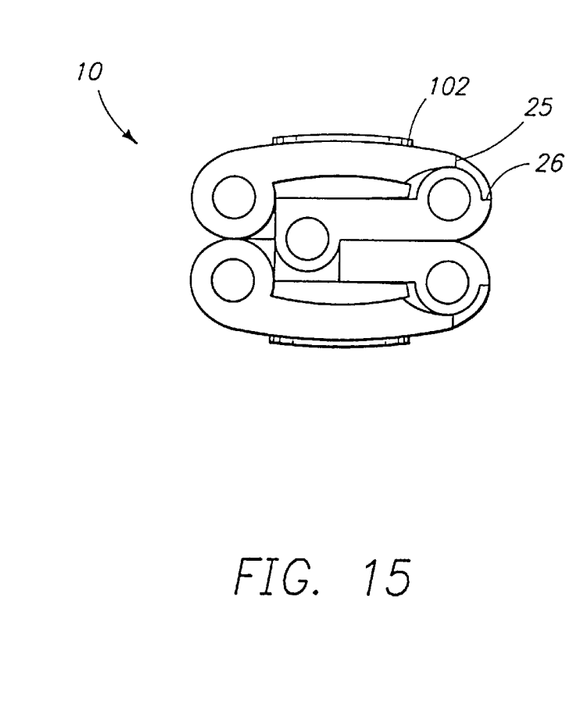
FIG. 15 is an end view of an alternate embodiment of a spinal fusion cage with an exaggerated raised edge.
Figure 16:
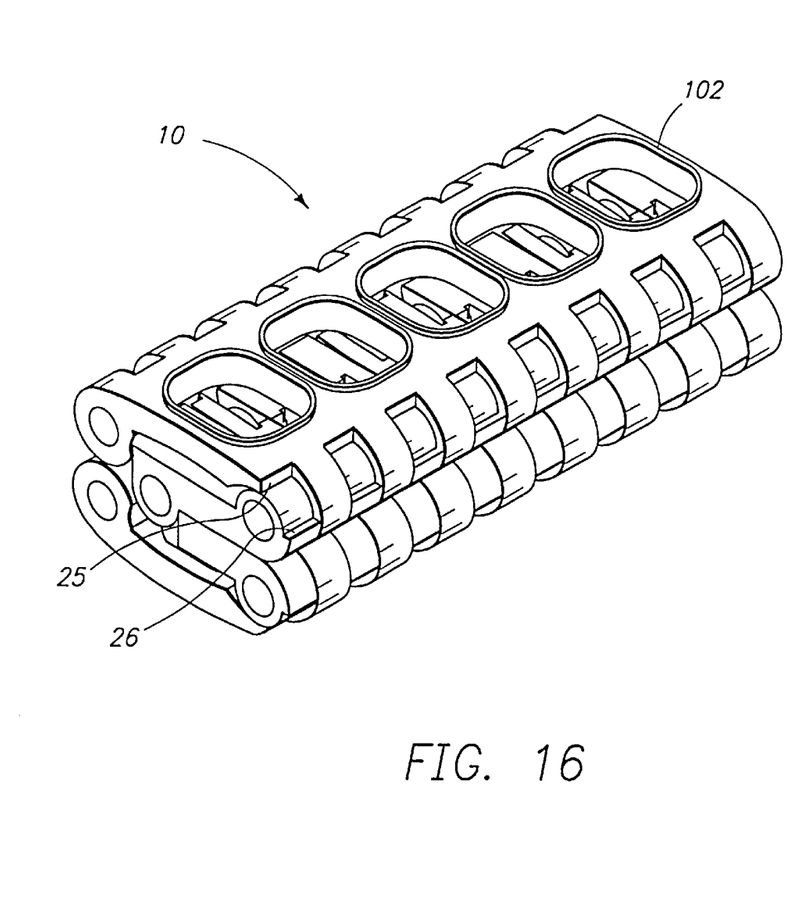
FIG. 16 is a perspective view of an alternate embodiment of a spinal fusion cage with an exaggerated raised edge.

In a preferred embodiment, each end of the assembled articulated support has a protrusion 96 adapted to assist in maintaining the fusion cage's position between vertebrae. It would also be possible to add protrusions, ridges, teeth, or other surface irregularities to the upper body 12 and the lower body 14 to aid in securing the fusion cage in place. For example, as shown in FIGS. 15 and 16, a raised edge 102 may be formed around the openings 22, 24. The protrusions, ridges, teeth, or other surface irregularities help to eliminate the need to drill and tap the vertebrae to accept the fusion cage, a process that is required with rigid threaded fusion cages.

In the fully expanded position, the articulated supports 16 and 18 have a slightly overcenter position. The upper body 12 has at least one stop 25 adapted to align with a support stop 26 on the articulated supports 16 and 18 to prevent further outward movement of the articulated supports 16 and 18 once the stops 25 and 26 are in contact. The stops 25 and 26 also act as a buttress to provide additional structural support once the fusion cage is fully opened. The pressure exerted on the fusion cage 10 by surrounding muscles, ligaments, and body weight forcing the adjacent vertebrae together forces the articulated supports 16 and 18 outward and holds them in the overcenter, stable, expanded position, thereby preventing the fusion cage 10 from collapsing.

Figures 17, 18:
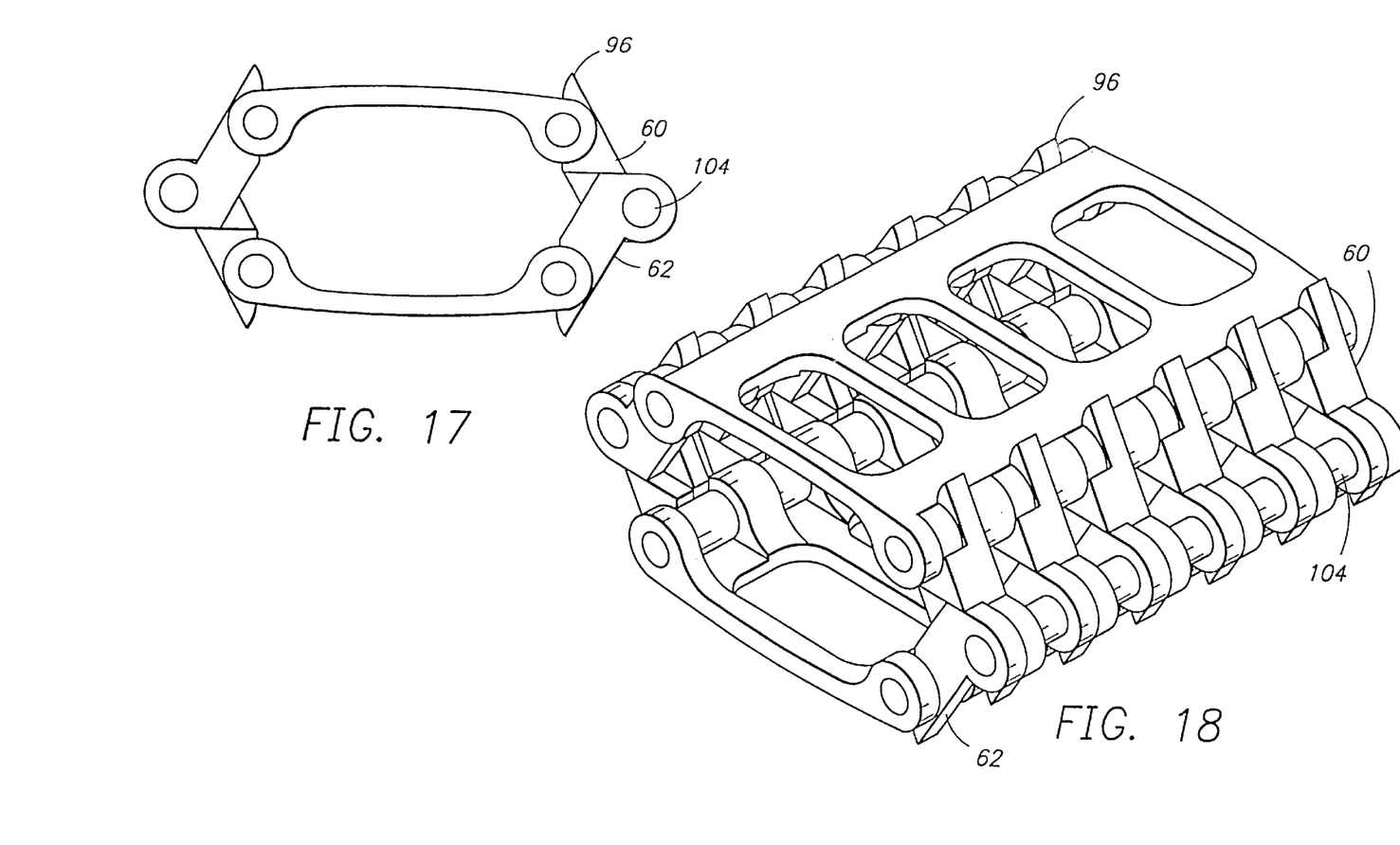
FIG. 17 is an end view of an alternative embodiment of the fusion cage in an exaggerated fully open position.
FIG. 18 is a perspective view of an alternative embodiment of the fusion cage in an exaggerated fully open position.

FIGS. 17 and 18 show an alternate preferred embodiment of the fusion cage with an exaggerated overcenter latch. Once the fusion cage is opened slightly past its maximum height, the buttressing formed by the shoulder stop 25 and the support stop 26 prevent the articulated supports from opening further and collapsing outward. The articulated supports 16, 18 are also prevented from collapsing outward by the engagement of the ledges 82, 86 with the shelves 80, 84. The buttressing can be provided at the interface between the articulated support and the upper or lower body, at the joint of the articulated support, or at both the interface and the joint.

The articulated supports are typically rigid. However, it would be possible to construct the articulated supports so as to provide a predetermined amount of flex. This added flexibility may affect the bone growth within the fusion cage. It would also be possible to introduce a flexible material between the joint of the upper and lower legs, or between the articulated supports and the upper or lower bodies.

As shown in the figures, the fusion cage is preferably symmetrical, having articulated supports of equal length. For some applications, however, it would be desirable for the legs to be a gradually decreasing length along the length of the fusion cage. This decrease would produce a tapered fusion cage. A tapered fusion cage according to the present invention could be used to address problems of kyphosis (hunch back) or lordosis (sway back). It would also be possible for the right-side articulated supports and the left-side articulated supports to be of different lengths, producing a fusion cage that is tapered side to side. The variability of the present invention allows for the treatment of a variety of conditions.

Although it is preferable for the articulated supports to stop once the fusion cage opens slightly past the maximum height, it would also be possible for the articulated supports to collapse outward. This embodiment would typically require an additional mechanism to maintain the fusion cage in its fully opened position.

Figure 3:
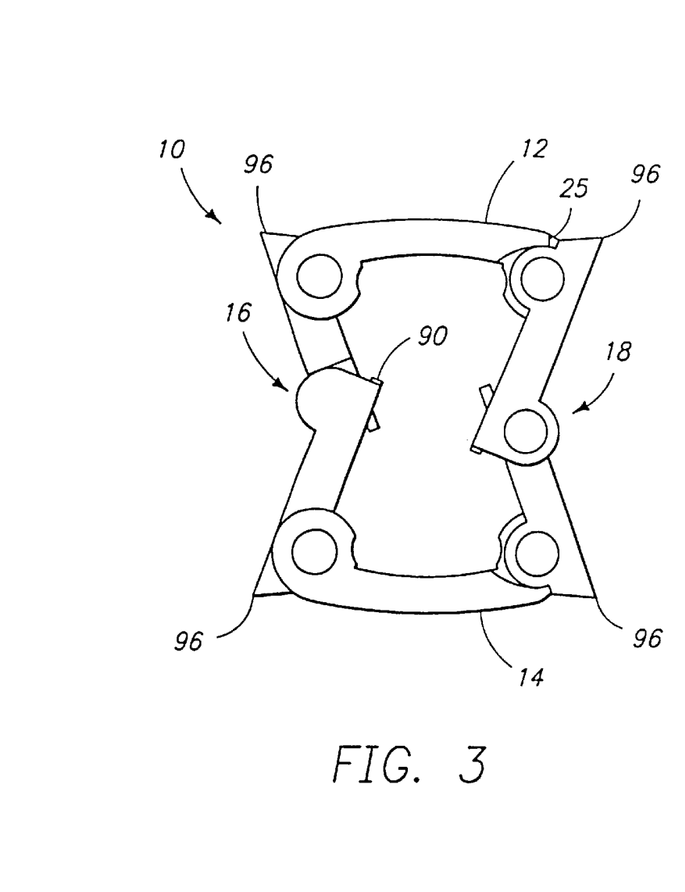
FIG. 3 is an end view of a spinal fusion cage in accordance with the present invention in a partially collapsed position.

In operation, the fusion cage 10 is inserted into a patient's body in the fully collapsed position, as shown in FIGS. 5 and 6. The interdigitated supports 16, 18 provide a minimal collapsed height relative to the expanded height. Once an opening has been made between adjacent vertebrae, the collapsed fusion cage 10 is inserted into the intervertebral disc space. The fusion cage 10 is then opened (as shown in FIGS. 3 and 4) until it reaches its maximum height (as shown in FIGS. 1 and 2). The protrusions 96 are forced upward into contact with the adjacent vertebrae to secure the fusion cage in place. The process may then be repeated on the opposite side of the disc space.

The foregoing disclosure and description thereof are for illustrative purposes only and are not intended to limit the invention. There may be many variations which will be apparent to a person of ordinary skill in the art upon reading this disclosure. This invention is defined by the claims, as interpreted by the rules of construction in patent cases.

I claim:
1. An interbody fusion cage comprising:
    a) an upper body and a lower body;
    b) at least one articulated support connecting said upper body to said lower body;
    c) an interior region defined by said upper body, said lower body, and said at least one articulated support; and
    d) said at least one articulated support having an expanded position and a collapsed position, said at least one articulated support folding inward toward the interior region as said at least one articulated support goes from said expanded position to said collapsed position.

2. The interbody fusion cage according to claim 1 wherein said at least one articulated support is a plurality of articulated supports.

3. The interbody fusion cage according to claim 1 wherein said at least one articulated support comprises an upper leg pivotally connected to a lower leg.

4. The interbody fusion cage according to claim 2 wherein said plurality of articulated supports are interdigitated in the collapsed position.

5. The interbody fusion cage according to claim 2 wherein said plurality of articulated supports comprises a first parallel row of articulated supports aligned with a second parallel row of articulated supports.

6. The interbody fusion cage according to claim 5 wherein said first and second parallel rows are collapsible towards each other.

7. The interbody fusion cage according to claim 5 wherein said first and second parallel rows are expandable away from each other.

8. An interbody fusion cage comprising:
   a) a first fusion cage plate;
   b) a second fusion cage plate;
   c) at least one inwardly collapsible articulated support having a first end, a second end, and at least one joint between said first end and said second end; and
   d) said first end of said at least one articulated support interconnected with said first fusion cage plate and said second end of said at least one articulated support interconnected with said second fusion cage plate.

9. The interbody fusion cage according to claim 8 wherein said at least one articulated support is a plurality of articulated supports.

10. The interbody fusion cage according to claim 9, said plurality of articulated supports each having an upper leg pivotally connected to a lower leg.

11. The interbody fusion cage according to claim 9 wherein said plurality of articulated supports are interdigitated in a collapsed position.

12. The interbody fusion cage according to claim 9 wherein said plurality of articulated supports comprises a first parallel row of articulated supports aligned with a second parallel row of articulated supports.

13. The interbody fusion cage according to claim 12 wherein said first and second parallel rows are collapsible towards each other.

14. The interbody fusion cage according to claim 12 wherein said first and second parallel rows are expandable away from each other.

15. A method for spacing adjacent portions of bone, said method comprising the steps of:
   a) providing a collapsible and expandable fusion cage having upper and lower bodies connected by at least one articulated support;
   b) collapsing said fusion cage to a collapsed position, said at least one articulated support collapsing inward;
   c) creating an opening to provide access between said adjacent portions of bone;
   d) inserting said fusion cage in said collapsed position through said opening into a space between said adjacent portions of bone; and
   e) expanding said fusion cage to an expanded position, said fusion cage supporting said adjacent portions of bone in a spaced relationship.

16. The method of claim 15 further comprising the steps of:
   a) providing a collapsible and expandable fusion cage;
   b) collapsing said second fusion cage to a collapsed position;
   c) inserting said fusion cage in said collapsed position through said opening into a space between said adjacent portions of bone; and
   d) expanding said fusion cage to an expanded position, said second fusion cage supporting said adjacent portions of bone in said spaced relationship.

17. A collapsible interbody fusion cage comprising:
   a) an upper body and a lower body;
   b) a plurality of articulated supports connecting said upper body to said lower body;
   c) an interior region defined by said upper body, said lower body, and said plurality of articulated supports; and
   d) said fusion cage having an expanded position and a collapsed position, said interior region being free from all elements of said fusion cage in said expanded position.

* * * * *

UNITED STATES PATENT AND TRADEMARK OFFICE
CERTIFICATE OF CORRECTION

PATENT NO. : 6,409,766 B1
DATED : June 25, 2002
INVENTOR(S) : Darrell C. Brett

It is certified that error appears in the above-identified patent and that said Letters Patent is hereby corrected as shown below:

Column 2,
Line 40, after "present" insert -- invention --.

Column 3,
Line 19, delete "case" and insert -- cage --.

Column 8,
Line 21, after "a" insert -- second --.
Lines 24 and 27, after "said" insert -- second --.

Signed and Sealed this

Thirty-first Day of May, 2005

JON W. DUDAS
*Director of the United States Patent and Trademark Office*